(12) United States Patent
Suzuki

(10) Patent No.: US 10,967,113 B2
(45) Date of Patent: Apr. 6, 2021

(54) DIALYSATE-EXTRACTING APPARATUS

(71) Applicant: Nikkiso Company Limited, Tokyo (JP)

(72) Inventor: Hiroaki Suzuki, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 263 days.

(21) Appl. No.: 15/812,507

(22) Filed: Nov. 14, 2017

(65) Prior Publication Data
US 2018/0071445 A1 Mar. 15, 2018

Related U.S. Application Data

(63) Continuation of application No. PCT/JP2016/064858, filed on May 19, 2016.

(30) Foreign Application Priority Data

May 19, 2015 (JP) .............................. JP2015-101702

(51) Int. Cl.
*A61M 1/16* (2006.01)
*A61M 1/36* (2006.01)
(Continued)

(52) U.S. Cl.
CPC .............. *A61M 1/168* (2013.01); *A61M 1/16* (2013.01); *A61M 1/1621* (2014.02);
(Continued)

(58) Field of Classification Search
None
See application file for complete search history.

(56) References Cited

U.S. PATENT DOCUMENTS 4,346,703 A 8/1982 Dennehey et al.
4,439,188 A 3/1984 Dennehey et al.
(Continued)

FOREIGN PATENT DOCUMENTS

EP 2737915 A1 6/2014
JP 55-099257 A 7/1980
(Continued)

OTHER PUBLICATIONS

International Search Report, application No. PCT/JP2016/064858 dated Jun. 14, 2016.
(Continued)

*Primary Examiner* — Krishnan S Menon
*Assistant Examiner* — Brad Gordon
(74) *Attorney, Agent, or Firm* — Young Basile Hanlon & MacFarlane, P.C.

(57) ABSTRACT

A dialysate-extracting apparatus in which a collecting port can be disinfected with no disinfecting work to be performed by a worker. A dialysate-extracting apparatus includes a dialysate-extracting device having an introduction port and a discharge port each of which is connected to the flow route for liquid and allows the liquid to flow therethrough, and a collecting port from which the liquid flowing in the flow route is collectable; and an opening-and-closing device that is movable between a closing position where the opening-and-closing device covers the collecting port of the dialysate-extracting device and an opening position where the opening-and-closing device 6 opens the collecting port. The dialysate-extracting apparatus further includes an ultraviolet-applying device attached to the opening-and-closing device and that is capable of applying ultraviolet rays to the collecting port when the opening-and-closing device is at the closing position.

10 Claims, 11 Drawing Sheets

(51) Int. Cl.
  *A61M 39/16* (2006.01)
  *A61M 1/34* (2006.01)
  *B01D 35/147* (2006.01)

(52) U.S. Cl.
  CPC ........ *A61M 1/1656* (2013.01); *A61M 1/3643* (2013.01); *A61M 39/16* (2013.01); *A61M 1/3455* (2013.01); *A61M 2039/167* (2013.01); *B01D 35/147* (2013.01)

(56) References Cited

U.S. PATENT DOCUMENTS

| | | | |
|---|---|---|---|
| 4,475,900 | A | 10/1984 | Popovich et al. |
| 9,192,708 | B2 | 11/2015 | Iwahori et al. |
| 9,579,445 | B2 | 2/2017 | Iwahori et al. |
| 2008/0053530 | A1 | 3/2008 | Knight et al. |
| 2010/0217179 | A1 | 8/2010 | Lo et al. |
| 2011/0146800 | A1* | 6/2011 | Jallon ................. E03C 1/00 137/1 |
| 2011/0172592 | A1 | 7/2011 | Lee |
| 2012/0321509 | A1* | 12/2012 | Bak .................. A61M 39/16 422/24 |
| 2013/0292313 | A1 | 11/2013 | Fava et al. |
| 2014/0138301 | A1 | 5/2014 | Iwahori et al. |
| 2014/0183114 | A1* | 7/2014 | Iwahori ............. A61M 1/3465 210/175 |
| 2014/0334974 | A1 | 11/2014 | Rasooly et al. |
| 2015/0021255 | A1 | 1/2015 | Takahashi et al. |
| 2017/0095602 | A1 | 4/2017 | Ishizaki et al. |
| 2017/0100530 | A1 | 4/2017 | Ishizaki et al. |

FOREIGN PATENT DOCUMENTS

| | | |
|---|---|---|
| JP | H03-73162 A | 3/1991 |
| JP | H05-049299 B2 | 7/1993 |
| JP | 2003/093501 A1 | 2/2003 |
| JP | 2004-313522 A | 11/2004 |
| JP | 2008-539992 A | 11/2008 |
| JP | 2009-207706 | 9/2009 |
| JP | 2010184029 A | 8/2010 |
| JP | 2011-161060 A | 8/2011 |
| JP | 2011-529728 B2 | 12/2011 |
| JP | 2013027495 A | 2/2013 |
| JP | 52-05496 B2 | 6/2013 |
| JP | 53-45614 B2 | 11/2013 |
| WO | 2006-122406 A1 | 11/2006 |
| WO | 2009/074588 A1 | 6/2009 |
| WO | 2013-015365 A | 1/2013 |
| WO | WO-2013035862 A1 * | 3/2013 ........... A61M 1/168 |
| WO | 2013/151114 A1 | 10/2013 |

OTHER PUBLICATIONS

Supplementary European Search Report dated Feb. 18, 2015 for application PCT/JP2012/068983.
Translation of International Search Report, Application No. PCT/JP2012/072976, dated Dec. 4, 2012.
European Search Report for Application No. 12830761.8 dated Apr. 10, 2015.
International Search Report from the Japanese Patent Office for Application No. PCT/JP2015/068561, dated Sep. 29, 2015.
Written Opinion from the Japanese Patent Office for Application No. PCT/JP2015/068561, dated Sep. 29, 2015.
Co-pending U.S. Appl. No. 14/163,051, filed Jan. 24, 2014, published as US 2014/0138301.
Co-pending U.S. Appl. No. 14/197,329, filed Mar. 5, 2014, granted as U.S. Pat. No. 9,192,708.
Co-pending U.S. Appl. No. 15/387,913, filed Dec. 22, 2016.
Co-pending U.S. Appl. No. 15/384,993, filed Dec. 22, 2016.
International Search Report from the Japanese Patent Office for Application No. PCT/JP2015/068562, dated Oct. 6, 2015.
Written Opinion from the Japanese Patent Office for Application No. PCT/JP2015/068562, dated Oct. 6, 2015.
Extended European Search Report, Application No. 13772926.5 dated Oct. 23, 2015.
Extended European Search Report dated Dec. 17, 2018, Application No. 16796554.0.

* cited by examiner

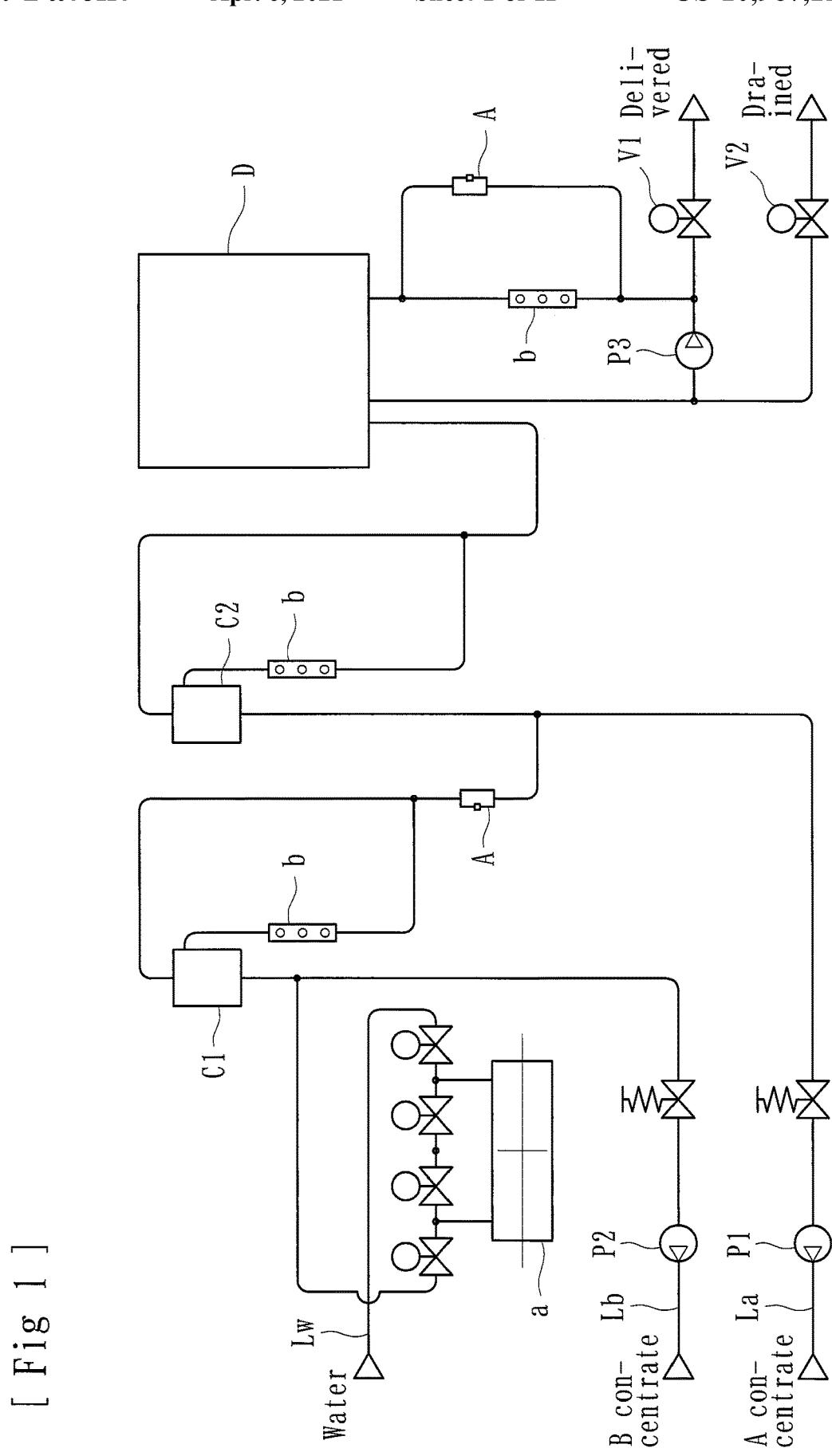
[Fig 1]

[Fig 2]
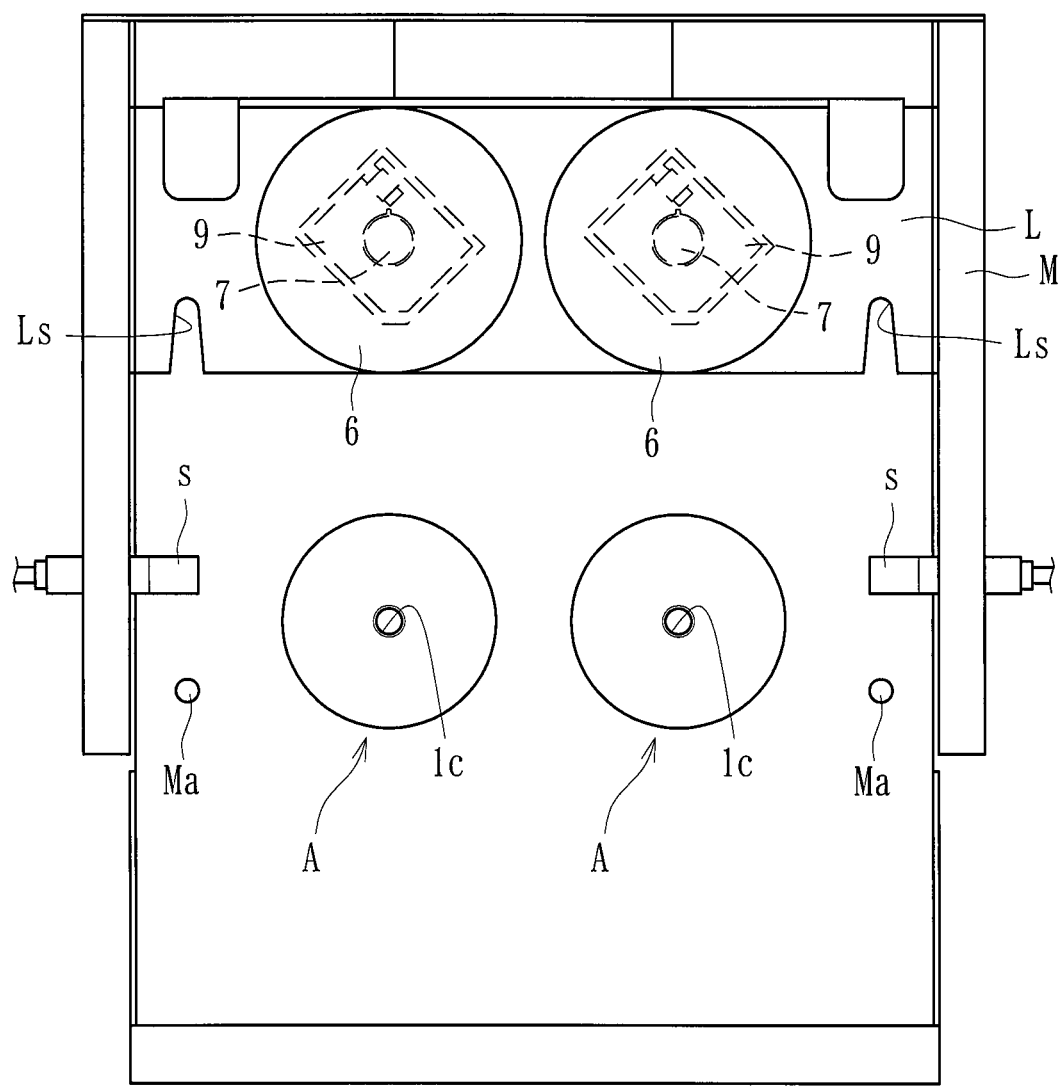

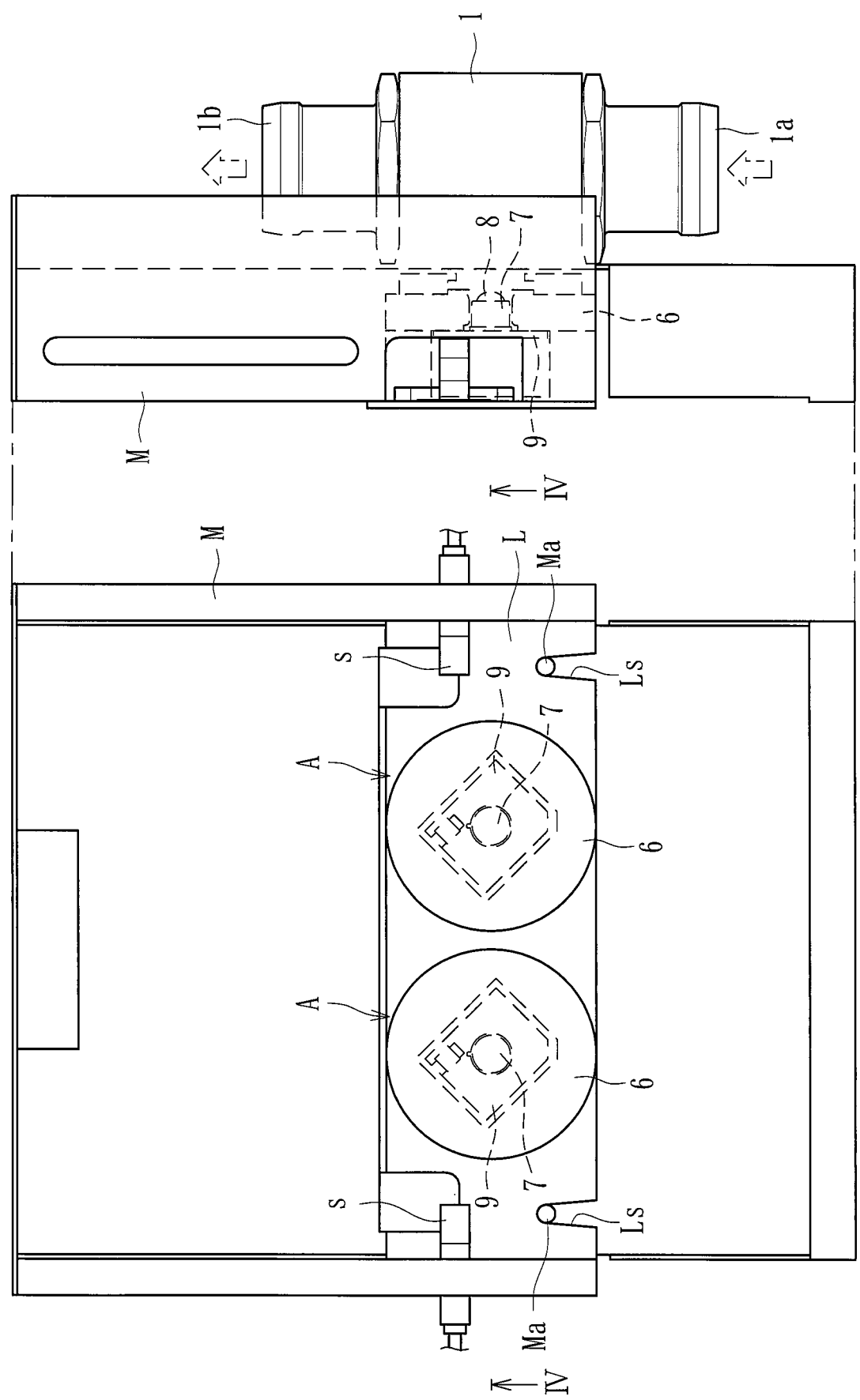

[Fig 4]
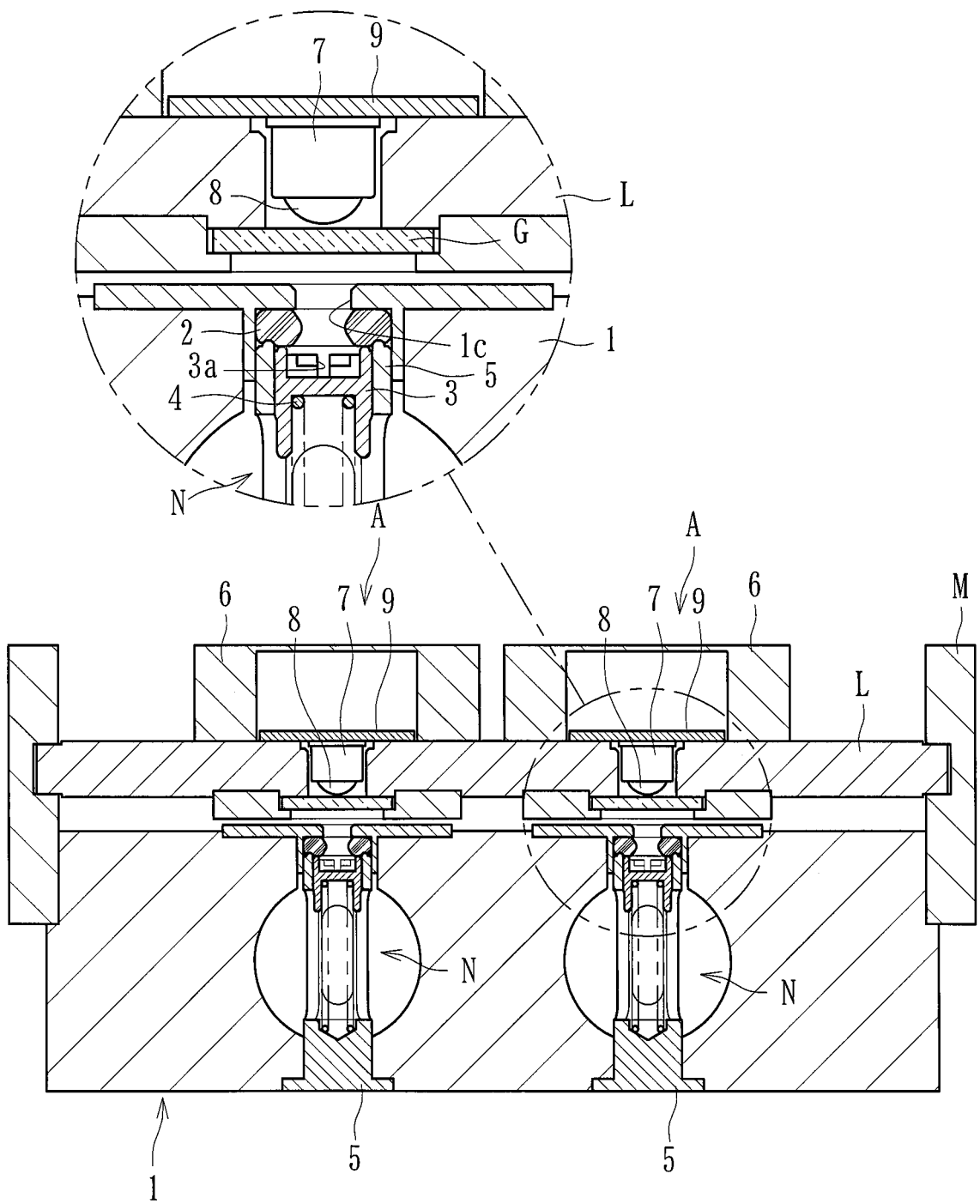

[Fig 5]
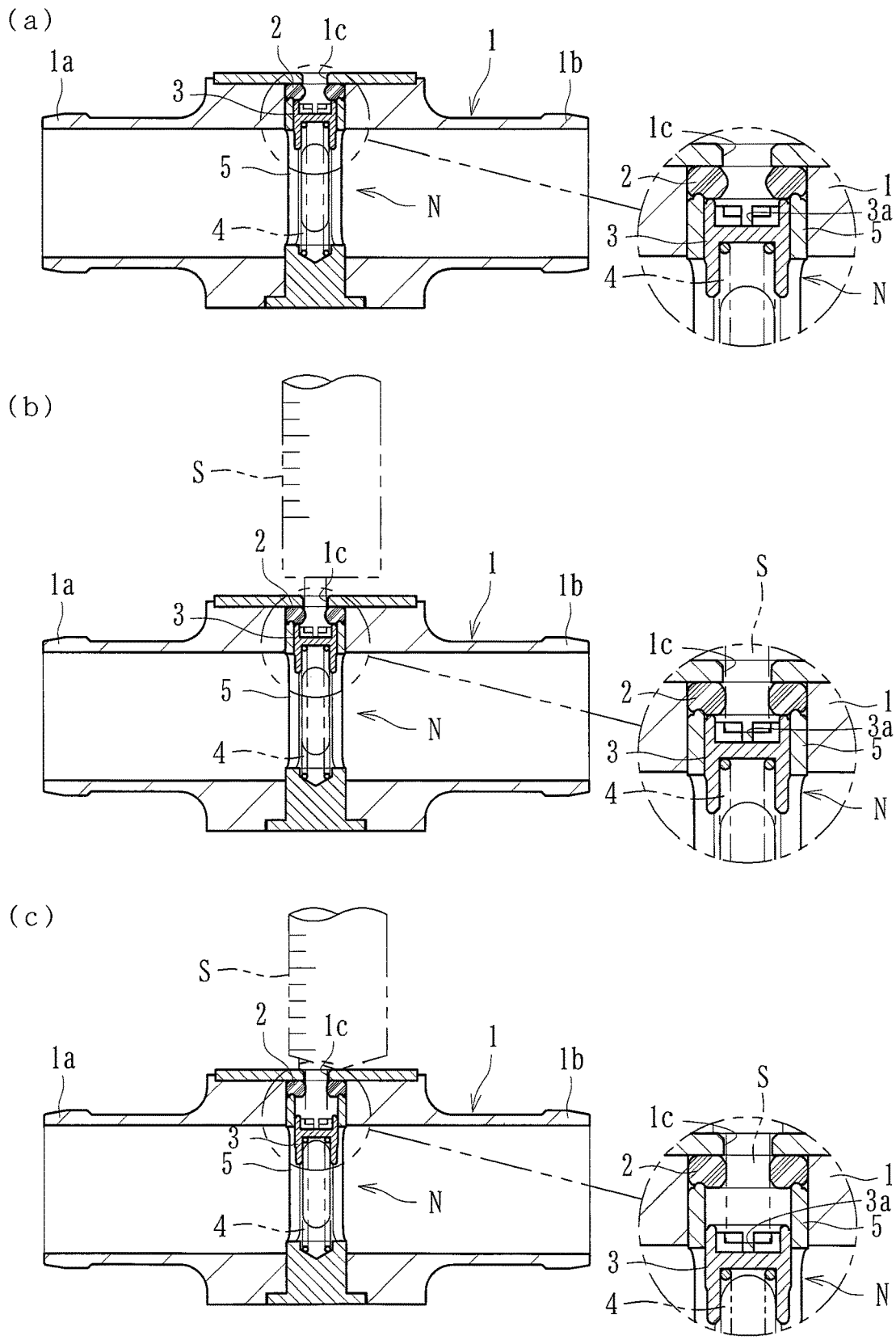

[Fig 6]
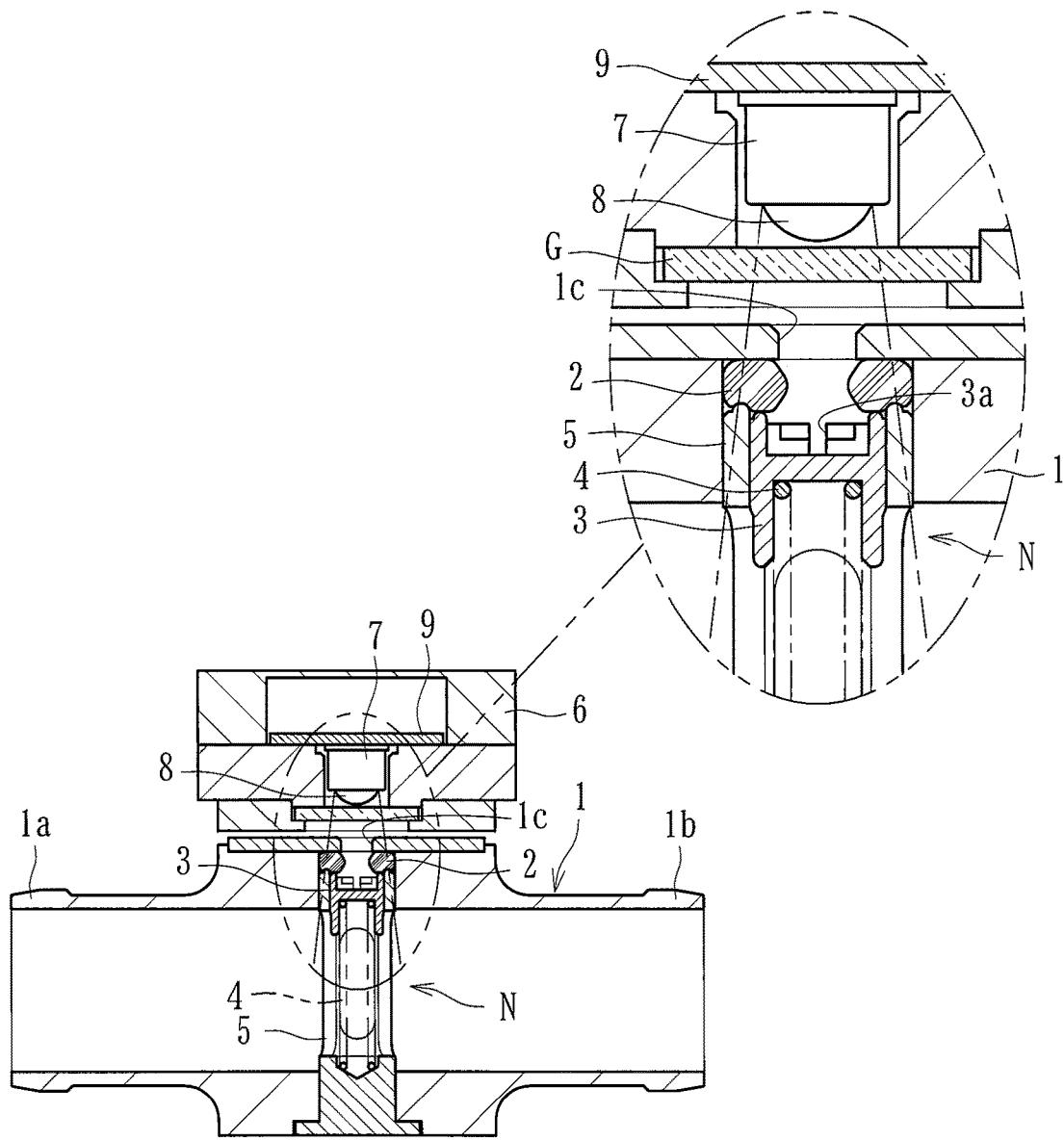

[Fig 7]
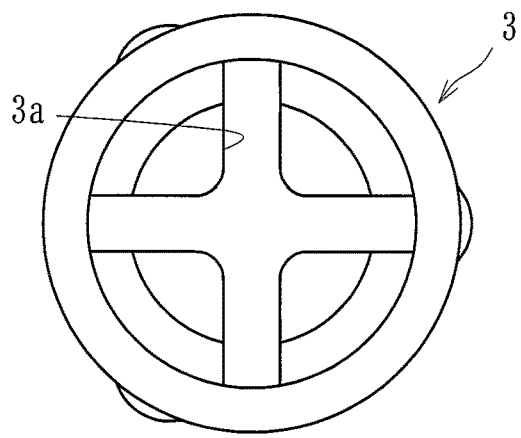
[Fig 8]
(a)
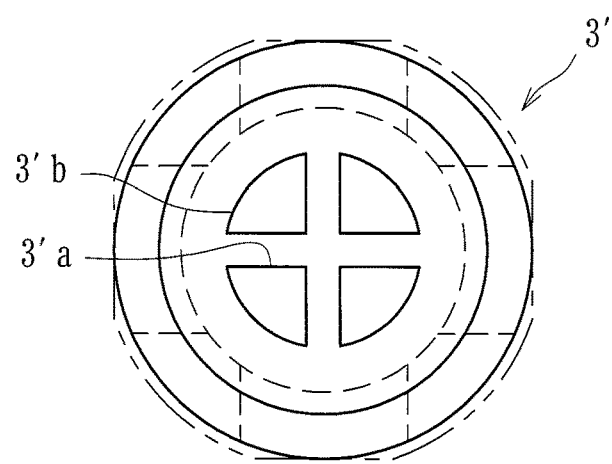
(b)
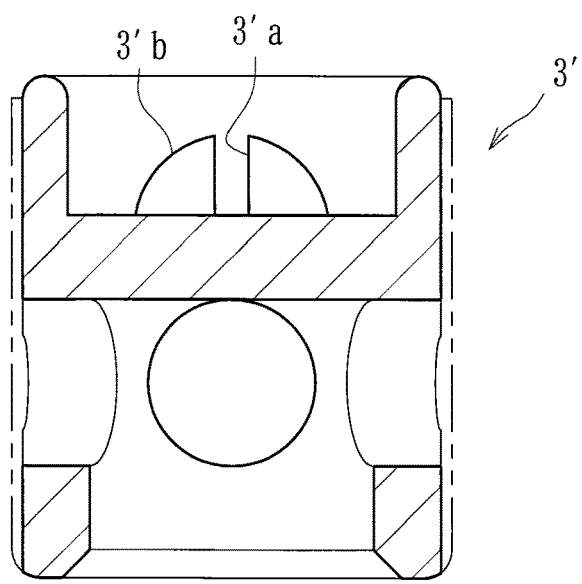

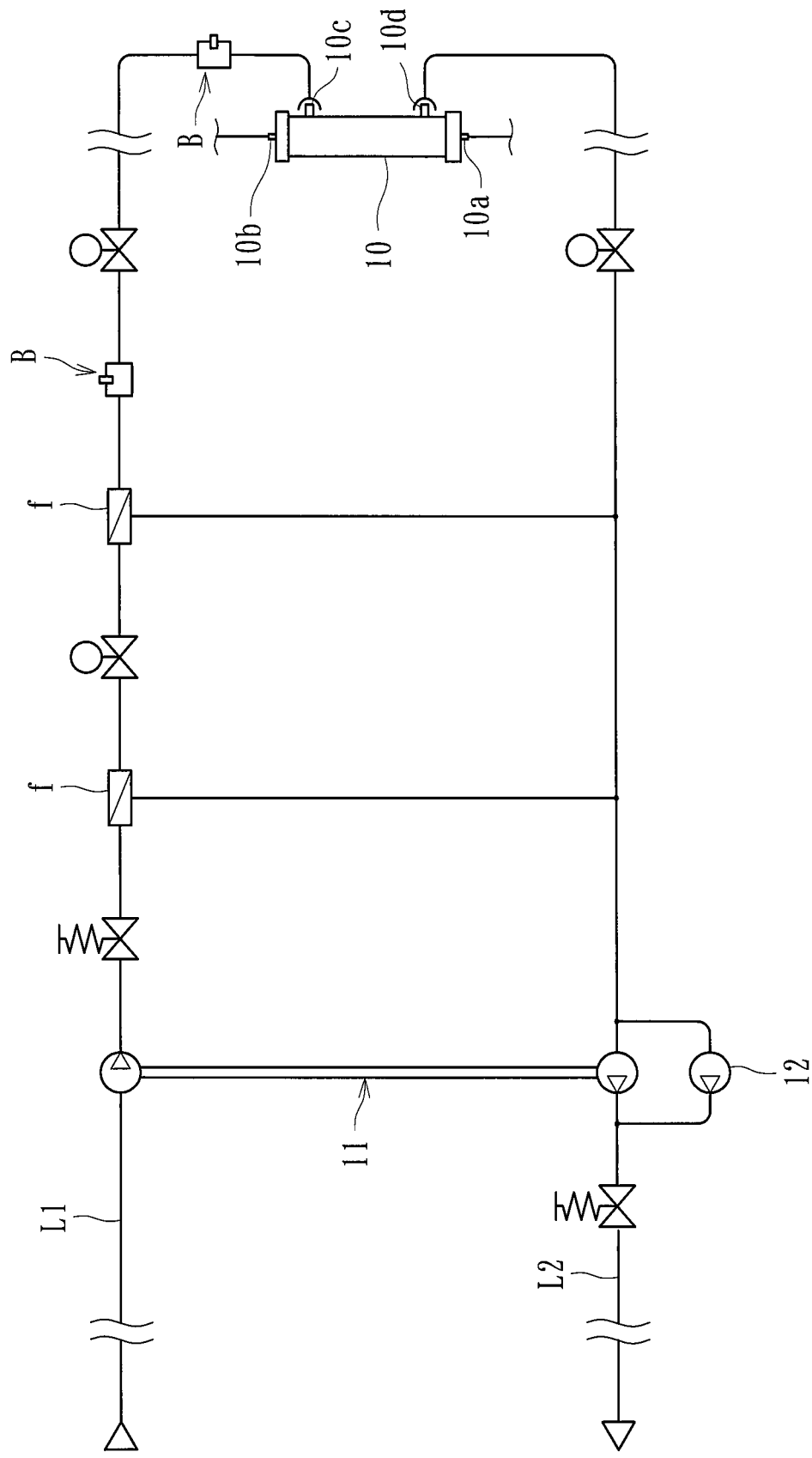

[ Fig 10 ]
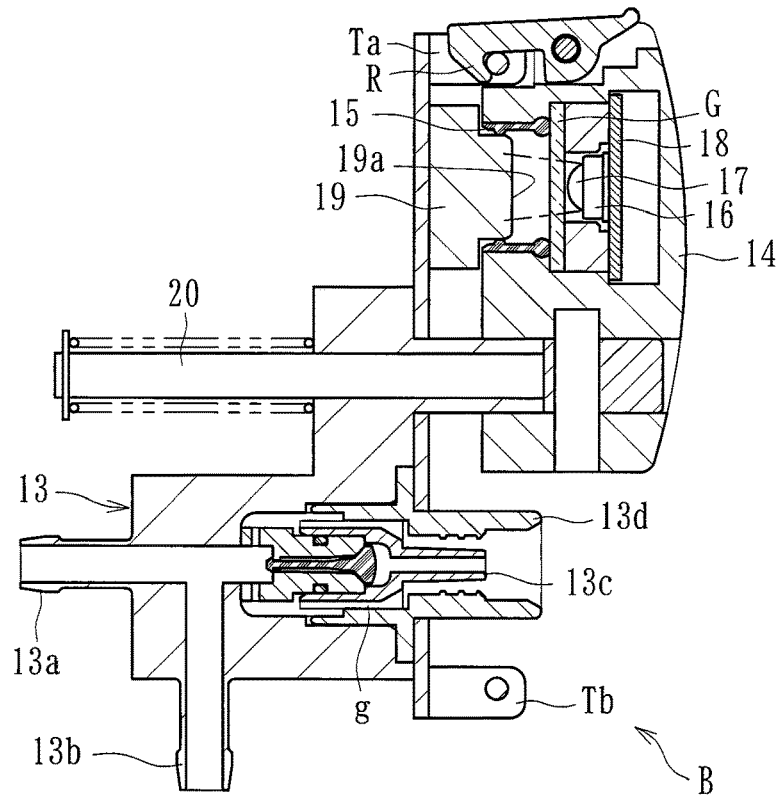
[ Fig 11 ]
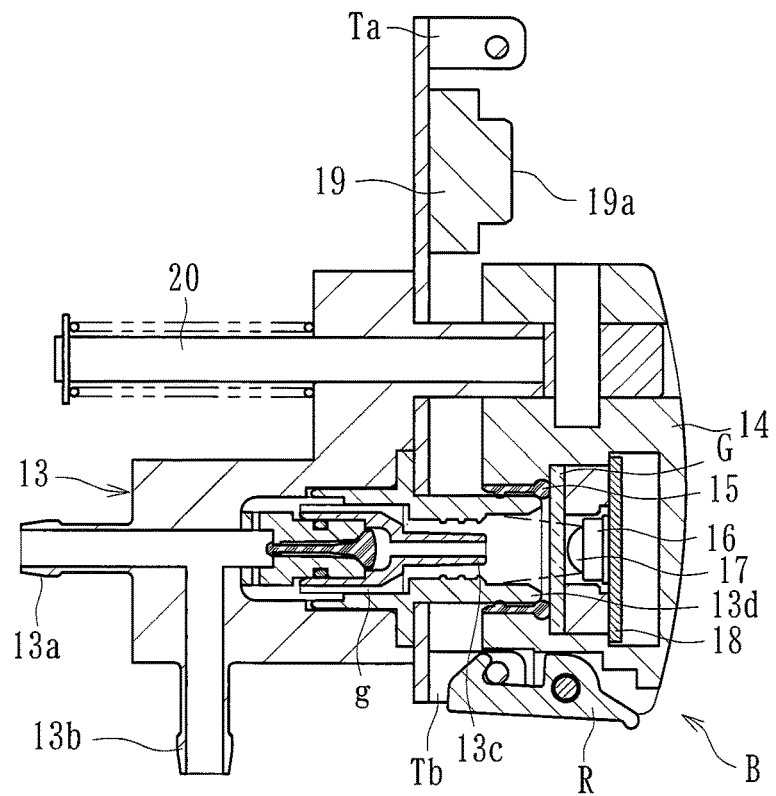

[ Fig 12 ]
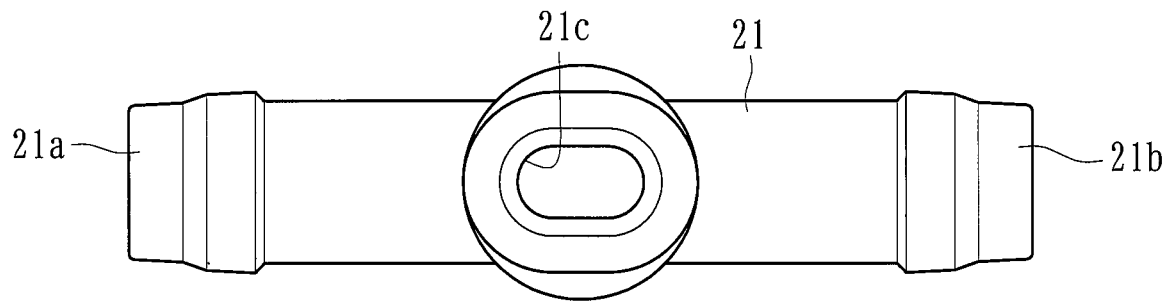
[ Fig 13 ]
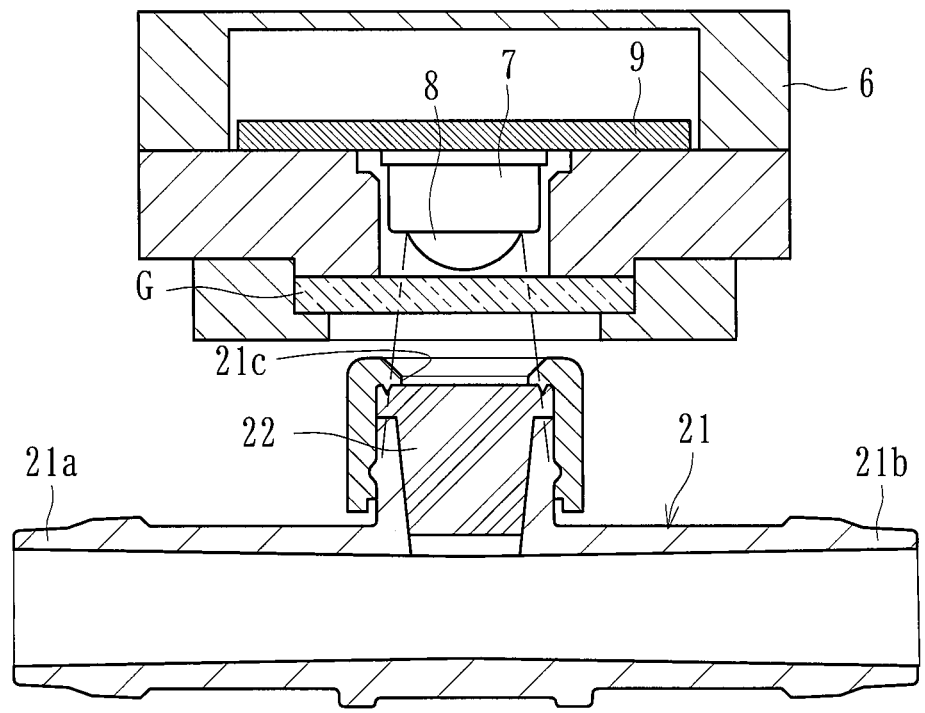

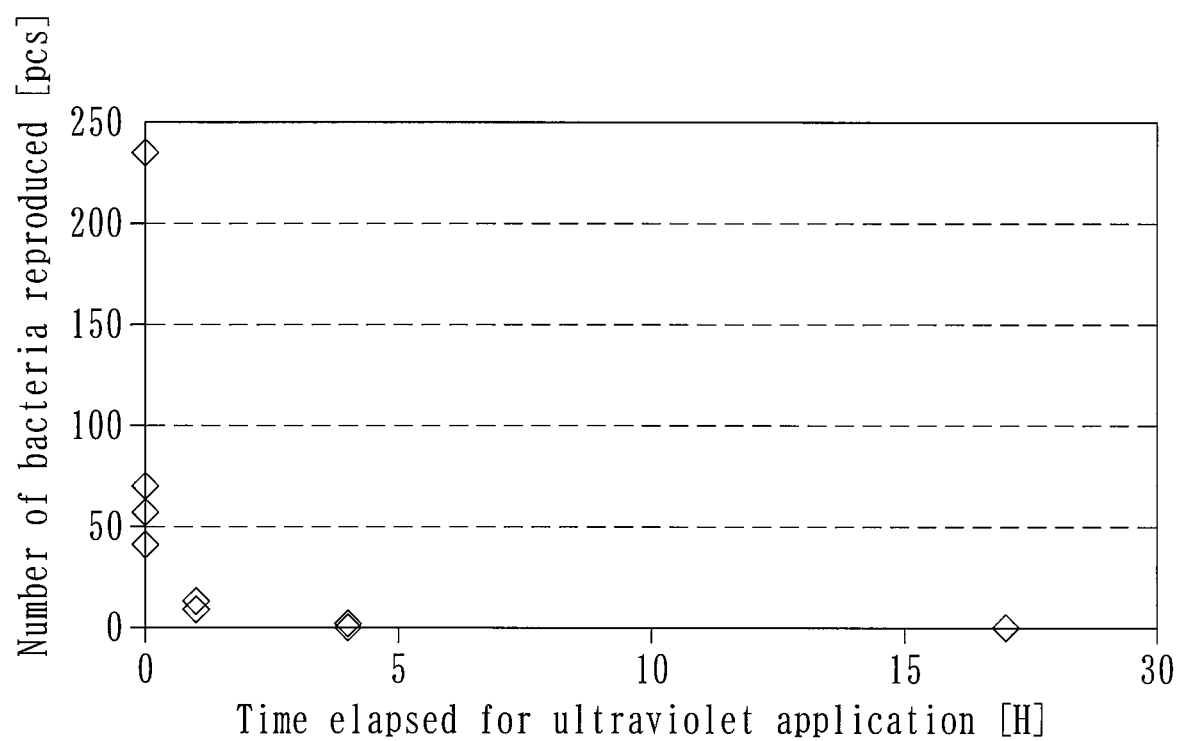
[Fig 14]

DIALYSATE-EXTRACTING APPARATUS

FIELD

The present teachings relate to a dialysate-extracting apparatus that includes a dialysate-extracting device having an introduction port and a discharge port each of which is connected to a flow route for liquid and allows the liquid to flow therethrough, and a collecting port from which the liquid flowing in the flow route is collectable; and an opening-and-closing device that is movable between a closing position where the opening-and-closing device covers the collecting port of the dialysate-extracting device and an opening position where the opening-and-closing device opens the collecting port.

BACKGROUND

Recently, some techniques for dialysis apparatuses serving as blood-purification apparatuses have been proposed, such as a technique of performing priming, blood returning, and substitution (emergency fluid infusion) by using dialysate that is supplied to a dialyzer when dialysis treatment (particularly, on-line HDF or on-line HF) is given, and a technique of using the dialysate as substitution fluid for the treatment of on-line HDF or on-line HF. An exemplary dialysis apparatus is disclosed by PTL 1 that includes a substitution line having one end thereof connected to a dialysate-extracting port (a collecting port) provided at a predetermined position of a dialysate introduction line and the other end thereof connected to a blood circuit (an arterial blood circuit or a venous blood circuit), and a substitution pump provided to the substitution line. To perform priming, blood returning, or substitution (emergency fluid infusion) in such a dialysis apparatus, the substitution pump is activated, whereby the dialysate in the dialysate introduction line is supplied to the blood circuit (the arterial blood circuit or the venous blood circuit).

Typically, the dialysate-extracting port is provided with a cap (an opening-and-closing device) detachably attached thereto. The cap is detached when the substitution line or the like is connected to the dialysate-extracting port. When the substitution line or the like is not connected to the dialysate-extracting port, the cap is attached to the port so that the dialysate flowing in the dialysate introduction line does not leak to the outside. For example, to wash or disinfect tubes such as the dialysate introduction line and the dialysate drain line through which the dialysate flows, washing water or disinfecting solution is made to flow through the tubes with the cap attached to the collecting port so that the washing water or the disinfecting solution is prevented from leaking to the outside.

When a syringe or a connection line is inserted into the collecting port, bacteria may adhere to the collecting port. To clean the collecting port, a worker such as a medical staff performs disinfecting work with alcohol or the like every time necessary. As with the case of the collecting port, the cap that is detachable from and attachable to the collecting port (particularly, a sealing unit for sealing the collecting port) is disinfected by a worker such as a medical staff with alcohol or the like every time necessary. Such disinfecting work takes some time. Under such circumstances, a technique for suppressing the propagation of bacteria has already been proposed in which the dialysate is constantly made to flow through the collecting port with the cap attached thereto (see PTL 2, for example).

PTL 1: Japanese Unexamined Patent Application Publication No. 2004-313522
PTL 2: Japanese Patent No. 5205496

SUMMARY

In the above known dialysate-extracting apparatus, although the propagation of bacteria is suppressed by causing the dialysate to constantly flow through the collecting port with the cap attached thereto, the collecting port cannot necessarily be disinfected. That is, a problem arises in that the effect of disinfection is not expected. Instead, there has been an increasing need for the disinfection of the collecting port with no disinfecting work to be performed by the worker.

The present teachings have been conceived in view of the above circumstances and provides a dialysate-extracting apparatus in which a collecting port can be disinfected with no disinfecting work to be performed by a worker.

According to the teachings herein, there is provided a dialysate-extracting apparatus that includes a dialysate-extracting device having an introduction port and a discharge port each of which is connected to a flow route for liquid and allows the liquid to flow therethrough, and a collecting port from which the liquid flowing in the flow route is collectable; and an opening-and-closing device that is movable between a closing position where the opening-and-closing device covers the collecting port of the dialysate-extracting device and an opening position where the opening-and-closing device opens the collecting port. The dialysate-extracting apparatus further comprises an ultraviolet-applying device attached to the opening-and-closing device and that is capable of applying ultraviolet rays to the collecting port when the opening-and-closing device is at the closing position.

According to the teachings herein, the dialysate-extracting apparatus taught herein further includes a sealing unit that seals the collecting port. Furthermore, the ultraviolet-applying device is capable of applying ultraviolet rays to the sealing unit.

According to the teachings herein, in the dialysate-extracting apparatus taught herein, the sealing unit includes a seal member provided around a peripheral edge of the collecting port, and a core member that seals the collecting port when coming into contact with the seal member and allows the liquid to be collected from the collecting port when moving away from the sealing member. Furthermore, the ultraviolet-applying device is capable of applying ultraviolet rays to the seal member and to the core member.

According to the teachings herein, in the dialysate-extracting apparatus taught herein, the core member is capable of transmitting the ultraviolet rays emitted from the ultraviolet-applying device or reflecting the ultraviolet rays around the core member.

According to the teachings herein, in the dialysate-extracting apparatus herein, the core member includes an adjusting portion that is capable of appropriately adjusting the reflection or transmission of the ultraviolet rays emitted from the ultraviolet-applying device.

According to the teachings herein, in the dialysate-extracting apparatus taught herein, the ultraviolet-applying device is an ultraviolet LED that is capable of emitting ultraviolet rays when energized.

According to the teachings herein, in the dialysate-extracting apparatus taught herein, an ultraviolet-emitting portion of the ultraviolet LED is provided with a lens that allows the ultraviolet rays to be diffused while being emitted.

According to the teachings herein, the dialysate-extracting apparatus includes the ultraviolet-applying device attached to the opening-and-closing device and that is capable of applying ultraviolet rays to the collecting port when the opening-and-closing device is at the closing position. Therefore, the collecting port can be disinfected with no disinfecting work to be performed by a worker.

According to the teachings herein, the dialysate-extracting apparatus further includes the sealing unit that seals the collecting port. Furthermore, the ultraviolet-applying device is capable of applying ultraviolet rays to the sealing unit. Therefore, not only the collecting port but also the sealing unit provided at the collecting port can be disinfected.

According to the teachings herein, the sealing unit includes the seal member provided around the peripheral edge of the collecting port, and the core member that seals the collecting port when coming into contact with the seal member and allows the liquid to be collected from the collecting port when moving away from the sealing member. Furthermore, the ultraviolet-applying device is capable of applying ultraviolet rays to the seal member and to the core member. Therefore, not only the collecting port but also the seal member and the core member that are provided at the collecting port can be disinfected.

According to the teachings herein, the core member is capable of transmitting the ultraviolet rays emitted from the ultraviolet-applying device or reflecting the ultraviolet rays around the core member. Therefore, the ultraviolet rays can be applied to desired sites around the core member.

According to the teachings herein, the core member includes the adjusting portion that is capable of appropriately adjusting the reflection or transmission of the ultraviolet rays emitted from the ultraviolet-applying device. Therefore, the ultraviolet rays can be more assuredly applied to desired sites around the core member.

According to the teachings herein, the ultraviolet-applying device is an ultraviolet LED that is capable of emitting ultraviolet rays when energized. Therefore, the ultraviolet-applying device can have a reduced size. Consequently, the ultraviolet-applying device is easy to attach to the opening-and-closing device and is easy to maintain.

According to the teachings herein, the ultraviolet-emitting portion of the ultraviolet LED is provided with the lens that allows the ultraviolet rays to be diffused while being emitted. Therefore, the ultraviolet rays from the ultraviolet LED can cover a more appropriate range.

BRIEF DESCRIPTION OF THE DRAWINGS

FIG. 1 is a diagram of a dialysate-generating apparatus to which a dialysate-extracting apparatus according to one embodiment of the present teachings are applied.

FIG. 2 is a plan view of the dialysate-extracting apparatus (with opening-and-closing devices being at an opening position).

FIG. 3 includes a plan view and a side view of the dialysate-extracting apparatus (with the opening-and-closing devices being at a closing position).

FIG. 4 is a sectional view taken along line IV-IV illustrated in FIG. 3.

FIG. 5 includes sectional views of a dialysate-extracting device included in the dialysate-extracting apparatus: part (a) illustrates a state where a collecting port is sealed by a sealing unit; part (b) illustrates a state where a syringe S is brought into contact with a core member; and part (c) illustrates a state where the sealing by the sealing unit is ended by pushing in the syringe S.

FIG. 6 is a sectional view illustrating a state where the collecting port of the dialysate-extracting device included in the dialysate-extracting apparatus is covered by the opening-and-closing device and ultraviolet rays are applied thereto.

FIG. 7 is a front view of a seal member included in the dialysate-extracting apparatus.

FIG. 8 includes schematic views of a seal member in another form: part (a) is a front view; and part (b) is a vertical sectional view.

FIG. 9 is a diagram of a blood purification apparatus to which a dialysate-extracting apparatus according to another embodiment of the present teachings are applied.

FIG. 10 is a sectional view of a dialysate-extracting device and an opening-and-closing device (at an opening position) included in the dialysate-extracting apparatus.

FIG. 11 is another sectional view of the dialysate-extracting device and the opening-and-closing device (at a closing position) included in the dialysate-extracting apparatus.

FIG. 12 is a plan view of a dialysate-extracting device included in a dialysate-extracting apparatus according to yet another embodiment of the present teachings.

FIG. 13 is a sectional view of the dialysate-extracting device and an opening-and-closing device (at a closing position) included in the dialysate-extracting apparatus.

FIG. 14 is a graph illustrating the effect of disinfection performed by an ultraviolet-applying device.

DETAILED DESCRIPTION

Embodiments of the present teachings will now be described specifically with reference to the drawings.

Dialysate-extracting apparatuses according to an embodiment are provided to a dialysate-supplying apparatus intended for preparing a dialysate at a predetermined concentration, which is obtained by mixing dialysis concentrates (an A drug and a B drug) together, and for supplying the dialysate to a dialysis apparatus. The dialysate-extracting apparatuses are each capable of collecting a corresponding one of a B concentrate and the dialysate prepared as above. As illustrated in FIG. 1, the applicable dialysate-supplying apparatus basically includes a water-supplying line Lw in which water flows and that is provided with a water-measuring device a that measures the amount of water, a concentrate line La provided with an infusion pump P1 and in which a dialysis concentrate (an A concentrate) obtained by dissolving the A drug flows, a concentrate line Lb provided with an infusion pump P2 and in which a dialysis concentrate (the B concentrate) obtained by dissolving the B drug flows, a mixing chamber C1 in which the water from the water-supplying line Lw and the B concentrate from the concentrate line Lb are allowed to be mixed together, a mixing chamber C2 in which the B concentrate having been mixed with the water in the mixing chamber C1 and the A concentrate from the concentrate line La are allowed to be mixed together, a storage tank D, and a liquid-delivering pump P3.

The dialysate thus prepared to have a predetermined concentration by flowing through the mixing chambers C1 and C2 is stored in the storage tank D. When the liquid-delivering pump P3 is activated with a liquid-delivering valve V1 being open, the dialysate in the storage tank D can be delivered to a dialysis apparatus installed in a treatment room. When a liquid-draining valve V2 is opened, the dialysate in the storage tank D can be discharged as drain liquid to the outside. Reference character b in FIG. 1 denotes a conductance cell for detecting the concentration of the liquid flowing therethrough.

Dialysate-extracting apparatuses A according to the present embodiment are provided to a flow route for the B concentrate mixed with water in the mixing chamber C1 and a flow route for the dialysate flowing from the storage tank D, respectively. Each dialysate-extracting apparatus A is capable of collecting the liquid flowing in the corresponding one of the flow routes. As illustrated in FIGS. 2 and 3, the dialysate-extracting apparatus A includes a dialysate-extracting device 1. The dialysate-extracting device 1 has an introduction port 1a and a discharge port 1b each of which is connected to the flow route for liquid (in the present embodiment, a corresponding one of the B concentrate and the dialysate prepared to have a predetermined concentration) and allows the liquid to flow therethrough, and a collecting port 1c from which the liquid flowing in the flow route is collectable. The dialysate-extracting apparatus A further includes an opening-and-closing device 6 that is movable between a closing position (see FIG. 3) where the opening-and-closing device 6 covers the collecting port 1c of the dialysate-extracting device 1 and an opening position (see FIG. 2) where the opening-and-closing device 6 opens the collecting port 1c.

The dialysate-extracting apparatuses A according to the present embodiment are provided with a base M to which the dialysate-extracting device 1 is attached, and a slide member L that is slidable with respect to the base M and to which the respective opening-and-closing devices 6 are attached. With the sliding of the slide member L, the opening-and-closing devices 6 are slidable between the closing position (the position in FIG. 3) where the opening-and-closing devices 6 cover the respective collecting ports 1c of the dialysate-extracting devices 1 and the opening position (FIG. 2) where the opening-and-closing devices 6 open the respective collecting ports 1c. The slide member L has a pair of cuts Ls. The base M has stoppers Ma that are fittable into the respective cuts Ls when the opening-and-closing devices 6 are at the closing position. When the slide member L is slid such that the cuts Ls are fitted onto the stoppers Ma, the opening-and-closing devices 6 cover the respective collecting ports 1c. The present embodiment employs sensors s that detect that the respective opening-and-closing devices 6 have been moved to the closing position with the sliding of the slide member L such that the cuts Ls are fitted onto the stoppers Ma.

As illustrated in FIGS. 4 and 5, each dialysate-extracting device 1 according to the present embodiment further includes a sealing unit N that seals the collecting port 1c. The sealing unit N includes a seal member 2 provided around the peripheral edge of the collecting port 1c, a core member 3 that seals the collecting port 1c when coming into contact with the seal member 2 and allows the liquid to be collected from the collecting port 1c when moving away from the seal member 2, a spring 4 that urges the core member 3 toward the seal member 2, and a supporting member 5 to which the spring 4 is attached and that allows the core member 3 to slide from the position where the core member 3 is in contact with the seal member 2 to the position where the core member 3 is spaced apart from the seal member 2.

The seal member 2 is an annular member fixed to the edge of a hole that is continuous with the collecting port 1c and through which the liquid flowing in the dialysate-extracting device 1 is allowed to be guided to the outside. The seal member 2 is made of, for example, resin, a rubber material, or the like. When the upper surface (a contact surface) of the core member 3 comes into contact with the back surface (the lower side in FIGS. 4 and 5) of the seal member 2, the collecting port 1c is closed and sealed. As illustrated in FIG. 7, the upper surface of the core member 3 has a cross-shaped groove 3a. As illustrated in part (b) and part (c) of FIG. 5, when the core member 3 is pushed in by the tip of a syringe S, the liquid in the dialysate-extracting device 1 can be collected through the groove 3a.

In the sealed state where the core member 3 is pressed against the seal member 2 with the urging force of the spring 4 (part (a) of FIG. 5), the tip of the syringe S is brought into contact with the upper surface of the core member 3 that is exposed to the outside from the collecting port 1c (part (b) of FIG. 5). Then, the syringe S is pushed into the collecting port 1c. Consequently, the core member 3 slides while being guided along the supporting member 5 against the urging force of the spring 4 (part (c) of FIG. 5). Thus, the core member 3 moves away from the seal member 2, and the sealing of the collecting port 1c is ended. Hence, the liquid in the dialysate-extracting device 1 can be collected with the syringe S.

As illustrated in FIGS. 4 and 6, the dialysate-extracting apparatus A according to the present embodiment includes an ultraviolet-applying device 7 attached to the opening-and-closing device 6 and that is capable of applying ultraviolet rays to the collecting port 1c when the opening-and-closing device 6 is at the closing position. The ultraviolet-applying device 7 is an ultraviolet LED that is capable of emitting ultraviolet rays when energized. An ultraviolet-emitting portion of the ultraviolet LED is provided with a lens 8 that allows the ultraviolet rays to be diffused while being emitted. The ultraviolet-applying device 7 is covered by a covering member G made of glass or the like for protection from water and drips. Reference numeral 9 in the drawings denotes a substrate on which the ultraviolet LED is mounted.

When a voltage is applied to the ultraviolet-applying device 7 so that ultraviolet rays are emitted, the ultraviolet rays reach the collecting port 1c and the sealing unit N (including the seal member 2, the core member 3, and so forth) through the lens 8. Thus, the collecting port 1c and the sealing unit N can be disinfected with the ultraviolet rays. The application of ultraviolet rays by the ultraviolet-applying device 7 is preferably performed continuously or intermittently when the opening-and-closing device 6 is at the closing position. Alternatively, the application may be performed only for a predetermined period of time after the opening-and-closing device 6 is moved to the closing position. Moreover, the application of ultraviolet rays by the ultraviolet-applying device 7 is preferably started if the sensor has detected that the opening-and-closing device 6 has been moved to the closing position with the sliding of the slide member L.

The present embodiment employs the ultraviolet-applying device 7 attached to the opening-and-closing device 6 and that is capable of applying ultraviolet rays to the collecting port 1c when the opening-and-closing device 6 is at the closing position. Therefore, the collecting port 1c can be disinfected with no disinfecting work to be performed by the worker. The present embodiment also employs the sealing unit N that seals the collecting port 1c. Furthermore, the ultraviolet-applying device 7 is capable of applying ultraviolet rays toward the sealing unit N. Therefore, not only the collecting port 1c but also the sealing unit N provided at the collecting port 1c can be disinfected.

The sealing unit N according to the present embodiment includes the seal member 2 provided around the peripheral edge of the collecting port 1c, and the core member 3 that seals the collecting port 1c when coming into contact with the seal member 2 and allows the liquid to be collectable from the collecting port 1c when moving away from the seal member 2. Furthermore, the ultraviolet-applying device 7 is capable of applying ultraviolet rays to the seal member 2 and to the core member 3. Therefore, not only the collecting port 1c but also the seal member 2 and the core member 3 provided at the collecting port 1c can be disinfected.

The core member 3 is preferably capable of transmitting the ultraviolet rays emitted from the ultraviolet-applying device 7 or reflecting the ultraviolet rays around the core member 3. For example, if the core member 3 is made of a transparent material such as silica glass, the core member 3 can transmit (or refract while transmitting) the ultraviolet rays. If the core member 3 is made of a material, such as metal, having a mirror surface and that is capable of reflecting ultraviolet rays, the ultraviolet rays can be reflected (or diffusedly reflected). Thus, the ultraviolet rays can be applied to desired sites around the core member 3 (for example, the back surface of the seal member 2, the part of the supporting member 5 along which the core member 3 slides, and so forth).

Moreover, a core member 3' illustrated in FIG. 8 may be employed. The core member 3' has an arc-shaped projection 3'b on the upper surface thereof with a cross-shaped groove 3'a provided in the projection 3'b. The projection 3'b serves as an adjusting portion that is capable of appropriately adjusting the reflection or transmission of the ultraviolet rays emitted from the ultraviolet-applying device 7. For example, the arc-shaped surface of the projection 3'b can appropriately adjust the angle of reflection of the ultraviolet rays or cause the ultraviolet rays transmitted therethrough to be refracted at a predetermined angle. Hence, the ultraviolet rays can be more assuredly applied to desired sites around the core member 3' (for example, the back surface of the seal member 2, the part of the supporting member 5 along which the core member 3 slides, and so forth).

In particular, since the ultraviolet-applying device 7 according to the present embodiment is an ultraviolet LED that is capable of emitting ultraviolet rays when energized, the ultraviolet-applying device 7 can have a reduced size. Therefore, the ultraviolet-applying device 7 is easy to attach to the opening-and-closing device 6 and is easier to maintain than an ultraviolet lamp or the like. Furthermore, since the ultraviolet-emitting portion of the ultraviolet LED is provided with the lens 8 that allows the ultraviolet rays to be diffused while being emitted, the ultraviolet rays from the ultraviolet LED can cover a more appropriate range.

Now, another embodiment of the present teachings will be described.

Dialysate-extracting apparatuses according to the present embodiment are provided to a blood purification apparatus intended for blood purification treatment (hemodialysis treatment) and are each capable of collecting dialysate. The applicable blood purification apparatus includes, as illustrated in FIG. 9, a dialyzer 10 (a blood purifier) connected to blood circuits (not illustrated), a dialysate introduction line L1 through which the dialysate can be introduced into the dialyzer 10, a dialysate drain line L2 through which drain liquid from the dialyzer 10 can be discharged, a duplex pump 11, and an ultrafiltration pump 12. Reference character f in FIG. 9 denotes a filtration filter provided to the dialysate introduction line L1.

The dialyzer 10 is intended for purifying blood that is extracorporeally circulated through the blood circuits and has connection ports 10a and 10b to which proximal ends of the respective blood circuits are connected, and connection ports 10c and 10d to which the dialysate introduction line L1 and the dialysate drain line L2 are connected, respectively. The duplex pump 11 is provided over the dialysate introduction line L1 and the dialysate drain line L2. The duplex pump 11 supplies the dialysate to the dialyzer 10 through the dialysate introduction line L1 while discharging the drain liquid from the dialyzer 10 through the dialysate drain line L2. The dialysate drain line L2 is provided with a bypass line that bypasses the duplex pump 11. The bypass line is provided with the ultrafiltration pump 12.

The dialysate introduction line L1 is provided with dialysate-extracting apparatuses B according to the another embodiment of the present teachings. As illustrated in FIGS. 10 and 11, each of the dialysate-extracting apparatuses B according to the present embodiment includes a dialysate-extracting device 13. The dialysate-extracting device 13 has an introduction port 13a and a discharge port 13b each of which is connected to the dialysate introduction line L1 (a flow route for liquid) and allows the liquid (dialysate) to flow therethrough, and a collecting port 13c from which the liquid flowing in the flow route is collectable. The dialysate-extracting apparatus B further includes an opening-and-closing device 14 and a seal member 15.

More specifically, the dialysate-extracting device B allows the dialysate to flow therethrough with the dialysate introduction line L1 connected to each of the introduction port 13a and the discharge port 13b. The flow route of the dialysate-extracting device B (a flow route in which the dialysate flows from the introduction port 13a toward the discharge port 13b) bends by about 90 degrees to form an L shape. The collecting port 13c and the introduction port 13a are positioned on one substantially straight line. A syringe, a connection line, or the like (not illustrated) is connected to the collecting port 13c with the opening-and-closing device 14 detached from the collecting port 13c. A wall portion 13d is formed around the collecting port 13c.

The opening-and-closing device 14 is movable between a closing position (see FIG. 11) where the opening-and-closing device 14 covers the collecting port 13c of the dialysate-extracting device 13 and an opening position (see FIG. 10) where the opening-and-closing device 14 opens the collecting port 13c. The opening-and-closing device 14 includes the seal member 15 and an ultraviolet-applying device 16. When the opening-and-closing device 14 is at the closing position as illustrated in FIG. 11, the seal member 15 can seal the periphery of the collecting port 13c (the inside of the wall portion 13d) by covering the outer peripheral surface of the wall portion 13d.

In the present embodiment, when the opening-and-closing device 14 is at the closing position, the liquid introduced from the introduction port 13a and ejected from the collecting port 13c flows into the sealed space provided on the inside of the wall portion 13d, flows through a flow route g, and is discharged from the discharge port 13b. Hence, even if the opening-and-closing device 14 is at the closing position, the dialysate is constantly allowed to flow through the collecting port 13c. Therefore, the propagation of bacteria can be suppressed.

The opening-and-closing device 14 according to the present embodiment is movable between the opening position (FIG. 10) and the closing position (FIG. 11) by being turned about a shaft member 20. The opening-and-closing device 14 is provided with a locking member R. When the openingand-closing device 14 is at the opening position, the locking member R engages with a locking-object member Ta, whereby the opening-and-closing device 14 can be locked at the opening position (see FIG. 10). When the opening-and-closing device 14 is at the closing position, the locking member R engages with a locking-object member Tb, whereby the opening-and-closing device 14 can be locked at the closing position (see FIG. 11).

The ultraviolet-applying device 16 according to the present embodiment is attached to the opening-and-closing device 14. When the opening-and-closing device 14 is at the closing position, the ultraviolet-applying device 16 is allowed to apply ultraviolet rays to the collecting port 13c. As in the above embodiment, the ultraviolet-applying device 16 is an ultraviolet LED that is capable of emitting ultraviolet rays when energized. An ultraviolet-emitting portion of the ultraviolet LED is provided with a lens 17 that allows the ultraviolet rays to be diffused while being emitted. Reference numeral 18 in the drawings denotes a substrate on which the ultraviolet LED is mounted.

When a voltage is applied to the ultraviolet-applying device 16 so that ultraviolet rays are emitted, the ultraviolet rays reach the collecting port 13c and the inside of the wall portion 13d through the lens 17. Thus, the collecting port 13c and the wall portion 13d can be disinfected with the ultraviolet rays. The application of ultraviolet rays by the ultraviolet-applying device 16 is preferably performed continuously or intermittently when the opening-and-closing device 14 is at the closing position. Alternatively, the application may be performed only for a predetermined period of time after the opening-and-closing device 14 is moved to the closing position.

A counter member 19 is fixed to a position that faces the ultraviolet-applying device 16 when the opening-and-closing device 14 is at the opening position. At least a surface 19a of the counter member 19 that is to face the ultraviolet-applying device 16 is mirror-finished. When the opening-and-closing device 14 is at the opening position, the ultraviolet rays from the ultraviolet-applying device 16 are reflected by the surface 19a and are applied to the opening-and-closing device 14 and to the seal member 15. Hence, the disinfection with the application of ultraviolet rays can be performed not only when the opening-and-closing device 14 is at the closing position but also when the opening-and-closing device 14 is at the opening position.

The effect of disinfection by the ultraviolet-applying device according to the present embodiment will now be described.

An experiment was conducted as follows. After liquid containing *Bacillus subtilis* was dropped onto the collecting port 1c of the dialysate-extracting device 1 according to the above embodiment illustrated in FIG. 6, the opening-and-closing device 6 illustrated in FIG. 6 was set to be in the closed state. Then, ultraviolet rays were emitted from the ultraviolet-applying device 7 (a process in which the application was continued for one second and was then withheld for ten seconds was repeated). The result of the experiment is graphed in FIG. 14, with the horizontal axis representing the time (H) elapsed for the application of ultraviolet rays and the vertical axis representing the number of bacteria reproduced (pcs). The experiment has showed that a great effect of disinfection is obtained by the application of ultraviolet rays as described in the embodiment. Note that the vertical axis represents the number of bacteria reproduced from those obtained by wiping, with a cotton swab, the collecting port 1c to which *Bacillus subtilis* was adhering and culturing them in a medium.

The present embodiment employs the ultraviolet-applying device 16 attached to the opening-and-closing device 14 and that is capable of applying ultraviolet rays to the collecting port 13c when the opening-and-closing device 14 is at the closing position. Therefore, the collecting port can be disinfected with no disinfecting work to be performed by the worker. In particular, since the ultraviolet-applying device 16 is an ultraviolet LED that is capable of emitting ultraviolet rays when energized, the ultraviolet-applying device 16 can have a reduced size. Therefore, the ultraviolet-applying device 16 is easy to attach to the opening-and-closing device and is easy to maintain. Furthermore, since the ultraviolet-emitting portion of the ultraviolet LED is provided with the lens 17 that allows the ultraviolet rays to be diffused while being emitted, the ultraviolet rays from the ultraviolet LED can cover a more appropriate range.

While some embodiments have been described above, the present teachings are not limited to such embodiments. For example, as illustrated in FIGS. 12 and 13, the present teachings may be applied to a dialysate-extracting device 21 that includes a sealing unit 22 having an introduction port 21a for introducing liquid, a discharge port 21b for discharging the liquid, and a collecting port 21c. The sealing unit 22 seals the collecting port 21c. The sealing unit 22 may be a silicon block or may be made of a rubber material or the like. In such a case also, when the opening-and-closing device 6 is at the closing position as illustrated in FIG. 13, ultraviolet rays are applied from the ultraviolet-applying device 7 attached to the opening-and-closing device 6 to the sealing unit 22, whereby the sealing unit 22 is disinfected.

While the ultraviolet-applying device according to each of the embodiments is an ultraviolet LED, the ultraviolet-applying device may be any other device (such as an ultraviolet lamp) that is capable of emitting ultraviolet rays, and may be provided with no lens 8 or 17 or the like. Moreover, the shape of the dialysate-extracting device, the position where the dialysate-extracting device is attached, the form of the opening-and-closing device, and other relevant factors may be different from those described above.

The present teachings are applicable to any dialysate-extracting apparatus having different features such as a different external shape or any additional functions, as long as the apparatus includes an ultraviolet-applying device attached to an opening-and-closing device and that is capable of applying ultraviolet rays to a collecting port when the opening-and-closing device is at a closing position.

REFERENCE SIGN LIST 1 dialysate-extracting device
2 seal member
3 core member
4 spring
5 supporting member
6 opening-and-closing device
7 ultraviolet-applying device
8 lens
9 substrate
10 dialyzer (blood purifier)
11 duplex pump
12 ultrafiltration pump
13 dialysate-extracting device
14 opening-and-closing device
15 seal member
16 ultraviolet-applying device
17 lens
18 substrate 19 counter member
20 shaft member
21 dialysate-extracting device
22 sealing unit

I claim:

1. A dialysate-extracting apparatus comprising:
a dialysate-extracting device having an introduction port and a discharge port each of which is configured to be connected to a flow route for liquid and allows the liquid to flow through the dialysate-extracting device, and a collecting port from which the liquid flowing in the flow route is collectable; and
an opening-and-closing device that is movable between a closing position where the opening-and-closing device covers the collecting port of the dialysate-extracting device and an opening position where the opening-and-closing device opens the collecting port;
a sealing unit that seals the collecting port, the sealing unit comprising:
a seal member provided around a peripheral edge of the collecting port; and
a core member that seals the collecting port when coming into contact with the seal member and allows the liquid to be collected from the collecting port when the core member is moving away from the sealing member;
an ultraviolet-applying device attached to the opening-and-closing device and that is capable of applying ultraviolet rays to the collecting port when the opening-and-closing device is at the closing position; the ultraviolet-applying device is capable of applying ultraviolet rays to the sealing unit; and the ultraviolet-applying device is capable of applying ultraviolet rays to the seal member and to the core member;
wherein the core member is capable of transmitting the ultraviolet rays emitted from the ultraviolet-applying device or reflecting the ultraviolet rays around the core member;
wherein the core member includes an adjusting portion that is capable of adjusting the reflection or transmission of the ultraviolet rays emitted from the ultraviolet-applying device;
wherein the core member has a projection with an arc-shaped surface that serves as the adjusting portion;
wherein the arc-shaped surface is configured to be adjustable so that an angle of the reflection or transmission of the ultraviolet rays relative to the ultraviolet-applying device are refracted at a predetermined angle and wherein the arc-shaped surface is further configured to apply the ultraviolet rays to one or more desired sites around the core member.

2. The dialysate-extracting apparatus according to claim 1, wherein the ultraviolet-applying device is an ultraviolet LED that is capable of emitting ultraviolet rays when energized.

3. The dialysate-extracting apparatus according to claim 2, wherein an ultraviolet-emitting portion of the ultraviolet LED is provided with a lens that allows the ultraviolet rays to be diffused while being emitted.

4. The dialysate-extracting apparatus according to claim 1, wherein the opening-and-closing device has a recess that covers the collecting port of the dialysate-extracting device so that the collecting port is protected by the opening-and-closing device when the opening-and-closing device is in the closing position.

5. The dialysate-extracting apparatus according to claim 4, wherein the ultraviolet-applying device is located within the recess of the opening-and-closing device so that when the collecting port extends over the opening-and-closing device, the ultraviolet rays from the ultraviolet-applying device are directed towards the collecting port.

6. The dialysate-extracting apparatus according to claim 1, wherein the ultraviolet-applying device is located in an internal location of and movable with the opening-and-closing device.

7. The dialysate-extracting apparatus according to claim 1, wherein the ultraviolet-applying device includes a lens.

8. The dialysate-extracting apparatus according to claim 1, wherein both the core member and the seal member are located within an internal location of the collecting port.

9. The dialysate-extracting apparatus according to claim 1, wherein a spring is in contact with the core member and the spring urges the core member towards the seal member.

10. The dialysate-extracting apparatus according to claim 1, wherein the sealing unit includes a supporting member to which the spring is attached and allows the core member to slide from a position where the core member is in contact with the seal member to a position where the core member is spaced apart from the seal member.

* * * * *